(12) United States Patent
Lehrberg et al.

(10) Patent No.: US 10,543,053 B2
(45) Date of Patent: Jan. 28, 2020

(54) CONTAINERS FOR MEDICAL DEVICES

(71) Applicant: PneumRx, Inc., Santa Clara, CA (US)

(72) Inventors: David Lehrberg, Redwood City, CA (US); Jeffrey W. Etter, Hayward, CA (US); Mark L. Mathis, Fremont, CA (US); Verna Rodriguez, Santa Cruz, CA (US)

(73) Assignee: PneumRx, Inc., Santa Clara, CA (US)

( * ) Notice: Subject to any disclaimer, the term of this patent is extended or adjusted under 35 U.S.C. 154(b) by 61 days.

(21) Appl. No.: 15/719,751

(22) Filed: Sep. 29, 2017

(65) Prior Publication Data
US 2018/0092704 A1 Apr. 5, 2018

Related U.S. Application Data

(60) Provisional application No. 62/402,730, filed on Sep. 30, 2016.

(51) Int. Cl.
*A61B 50/30* (2016.01)
*A61B 17/12* (2006.01)
(Continued)

(52) U.S. Cl.
CPC ........ *A61B 50/30* (2016.02); *A61B 17/12104* (2013.01); *A61B 17/12145* (2013.01);
(Continued)

(58) Field of Classification Search
CPC ................................ A61B 50/30; A61B 17/12
(Continued)

(56) References Cited

U.S. PATENT DOCUMENTS

| 4,257,521 A | 3/1981 | Poler |
| 4,721,123 A | 1/1988 | Cosentino et al. |

(Continued)

FOREIGN PATENT DOCUMENTS

| WO | 2004110295 | 12/2004 |
| WO | 2006035423 | 4/2006 |
| WO | 2009020836 | 2/2009 |

OTHER PUBLICATIONS

PneumRx Lung vol. Reduction Devices (LVRD) Instructions for Use, 2007, 8 pages.
(Continued)

*Primary Examiner* — J. Gregory Pickett
*Assistant Examiner* — Tia Cox
(74) *Attorney, Agent, or Firm* — Kilpatrick Townsend & Stockton LLP

(57) ABSTRACT

A container for a medical device having a housing defining a cavity for receiving a device, such as a lung volume reduction coil, is disclosed. In some embodiments, the container includes a coupling zone external to the cavity, an exit aperture between the cavity and the coupling zone, and a bearing surface located within the cavity, the bearing surface, exit aperture and coupling zone defining an exit path along which the device can be moved for deployment from the container. The bearing surface is spaced from the exit aperture and arranged, together with the coupling zone, such that the exit path is substantially straight. In some embodiments, the cavity may be approximately cylindrical, and the bearing surface, the exit aperture, and the coupling zone are aligned such that the exit path extends in a direction that is substantially tangential to the cavity.

24 Claims, 16 Drawing Sheets

(51) Int. Cl.
*B65D 8/02* (2006.01)
*B65D 85/04* (2006.01)
*A61B 50/00* (2016.01)
*A61B 17/28* (2006.01)

(52) U.S. Cl.
CPC .............. *B65D 11/08* (2013.01); *B65D 85/04* (2013.01); *A61B 17/28* (2013.01); *A61B 2017/1205* (2013.01); *A61B 2050/0067* (2016.02)

(58) Field of Classification Search
USPC ....... 206/364, 438, 389, 408, 804, 571, 363, 206/564, 409, 63.3
See application file for complete search history.

(56) References Cited

U.S. PATENT DOCUMENTS

| | | | |
|---|---|---|---|
| 4,773,432 A | | 9/1988 | Rydell |
| 4,917,102 A | | 4/1990 | Miller et al. |
| 5,054,501 A | | 10/1991 | Chuttani et al. |
| 5,333,620 A | | 8/1994 | Moutafis et al. |
| 5,344,011 A | * | 9/1994 | DiBernardo ........ A61M 25/002 206/364 |
| 5,447,148 A | * | 9/1995 | Oneda ................ A61B 1/00091 600/131 |
| 5,738,213 A | * | 4/1998 | Whiting .............. A61M 25/002 206/210 |
| 5,769,222 A | * | 6/1998 | Banerian ............. A61M 25/002 206/210 |
| 5,848,691 A | * | 12/1998 | Morris ................ A61M 25/002 206/364 |
| 5,890,594 A | * | 4/1999 | Hansen ................ B65D 75/245 206/216 |
| 6,174,323 B1 | | 1/2001 | Biggs et al. |
| 6,183,420 B1 | | 2/2001 | Douk et al. |
| 6,371,928 B1 | | 4/2002 | Mcfann et al. |
| 6,409,682 B1 | | 6/2002 | Burmeister et al. |
| 6,459,921 B1 | | 10/2002 | Belef et al. |
| 6,514,290 B1 | | 2/2003 | Loomas |
| 6,599,311 B1 | | 7/2003 | Biggs et al. |
| 6,669,652 B2 | | 12/2003 | Anderson et al. |
| 6,716,183 B2 | | 4/2004 | Clayman et al. |
| 6,997,189 B2 | | 2/2006 | Biggs et al. |
| 7,115,101 B2 | | 10/2006 | Cornelius et al. |
| 7,468,350 B2 | | 12/2008 | Gong et al. |
| 7,549,984 B2 | | 6/2009 | Mathis |
| 7,553,810 B2 | | 6/2009 | Gong et al. |
| 7,595,082 B2 | | 9/2009 | Connors, III et al. |
| 7,608,579 B2 | | 10/2009 | Gong et al. |
| 7,670,282 B2 | | 3/2010 | Mathis |
| 7,678,767 B2 | | 3/2010 | Gong et al. |
| 7,766,938 B2 | | 8/2010 | McGurk et al. |
| 7,775,968 B2 | | 8/2010 | Mathis |
| 7,883,474 B1 | | 2/2011 | Mirigian et al. |
| 7,932,225 B2 | | 4/2011 | Gong et al. |
| 8,142,455 B2 | | 3/2012 | Thompson et al. |
| 8,157,823 B2 | | 4/2012 | Aronson et al. |
| 8,157,837 B2 | | 4/2012 | Thompson et al. |
| 8,282,660 B2 | | 10/2012 | Thompson et al. |
| 8,413,811 B1 | | 4/2013 | Arendt |
| 8,431,537 B2 | | 4/2013 | Gong et al. |
| 8,632,605 B2 | | 1/2014 | Thompson et al. |
| 8,668,707 B2 | | 3/2014 | Thompson et al. |
| 8,721,734 B2 | | 5/2014 | Mathis et al. |
| 8,888,800 B2 | | 11/2014 | Mathis et al. |
| 8,911,465 B2 | | 12/2014 | Mathis et al. |
| 8,932,310 B2 | | 1/2015 | Thompson et al. |
| 9,125,639 B2 | | 9/2015 | Mathis et al. |
| 9,173,669 B2 | | 11/2015 | Mathis et al. |
| 9,192,403 B2 | | 11/2015 | Aronson et al. |
| 9,402,632 B2 | | 8/2016 | Mathis et al. |
| 9,402,633 B2 | | 8/2016 | Vasquez et al. |
| RE46,209 E | | 11/2016 | Gong et al. |
| 2005/0281739 A1 | | 12/2005 | Gong et al. |
| 2005/0281740 A1 | | 12/2005 | Gong et al. |
| 2005/0281796 A1 | | 12/2005 | Gong et al. |
| 2005/0281798 A1 | | 12/2005 | Gong et al. |
| 2005/0281799 A1 | | 12/2005 | Gong et al. |
| 2005/0281800 A1 | | 12/2005 | Gong et al. |
| 2005/0288684 A1 | | 12/2005 | Aronson et al. |
| 2005/0288702 A1 | | 12/2005 | McGurk et al. |
| 2006/0004400 A1 | | 1/2006 | McGurk et al. |
| 2006/0025815 A1 | | 2/2006 | McGurk et al. |
| 2008/0021405 A1 | | 1/2008 | Jacobsen et al. |
| 2008/0257377 A1 | | 10/2008 | Burrows |
| 2008/0312543 A1 | | 12/2008 | Laufer et al. |
| 2009/0131765 A1 | | 5/2009 | Roschak et al. |
| 2010/0297218 A1 | | 11/2010 | Gong et al. |
| 2012/0259403 A1 | * | 10/2012 | Hendriksen ................ A61F 2/95 623/1.12 |
| 2012/0265100 A1 | | 10/2012 | Maki |
| 2012/0330226 A1 | * | 12/2012 | Lee .................. A61B 17/12022 604/60 |
| 2013/0096603 A1 | | 4/2013 | Mathis et al. |
| 2013/0103059 A1 | | 4/2013 | Mathis et al. |
| 2013/0184579 A1 | | 7/2013 | Roschak et al. |
| 2014/0073588 A1 | | 3/2014 | Gong et al. |
| 2014/0371705 A1 | | 12/2014 | Thompson et al. |
| 2015/0051709 A1 | * | 2/2015 | Vasquez .......... A61B 17/12104 623/23.65 |
| 2015/0073563 A1 | | 3/2015 | Mathis et al. |
| 2015/0080934 A1 | | 3/2015 | Aronson et al. |
| 2015/0119920 A1 | * | 4/2015 | Mathis ............. A61B 17/12145 606/191 |
| 2015/0142035 A1 | | 5/2015 | Mathis et al. |
| 2015/0328435 A1 | | 11/2015 | Mathis et al. |
| 2016/0113657 A1 | | 4/2016 | Mathis et al. |
| 2017/0027584 A1 | | 2/2017 | Vasquez et al. |
| 2017/0027585 A1 | | 2/2017 | Mathis et al. |
| 2017/0065282 A1 | | 3/2017 | Mathis et al. |
| 2017/0156732 A1 | | 6/2017 | Lehrberg et al. |
| 2018/0028193 A1 | | 2/2018 | Mathis et al. |
| 2018/0064411 A1 | | 3/2018 | Roschak et al. |

OTHER PUBLICATIONS

PneumRx RePneu Coil System Instructions for Use, Dec. 2014, pp. 1-8.
PneumRx RePneu Lung Volume Reduction Coil (LVRC) Instructions for Use, 2010, pp. 1-8.
PneumRx RePneu Lung Volume Reduction Coil (LVRC) System Instructions for Use, Jun. 2015, pp. 1-8.
PneumRx, Inc., RePneu Lung Volume Reduction Coil (LVRC) System Instructions for Use, Feb. 2014, pp. 1-8.

\* cited by examiner

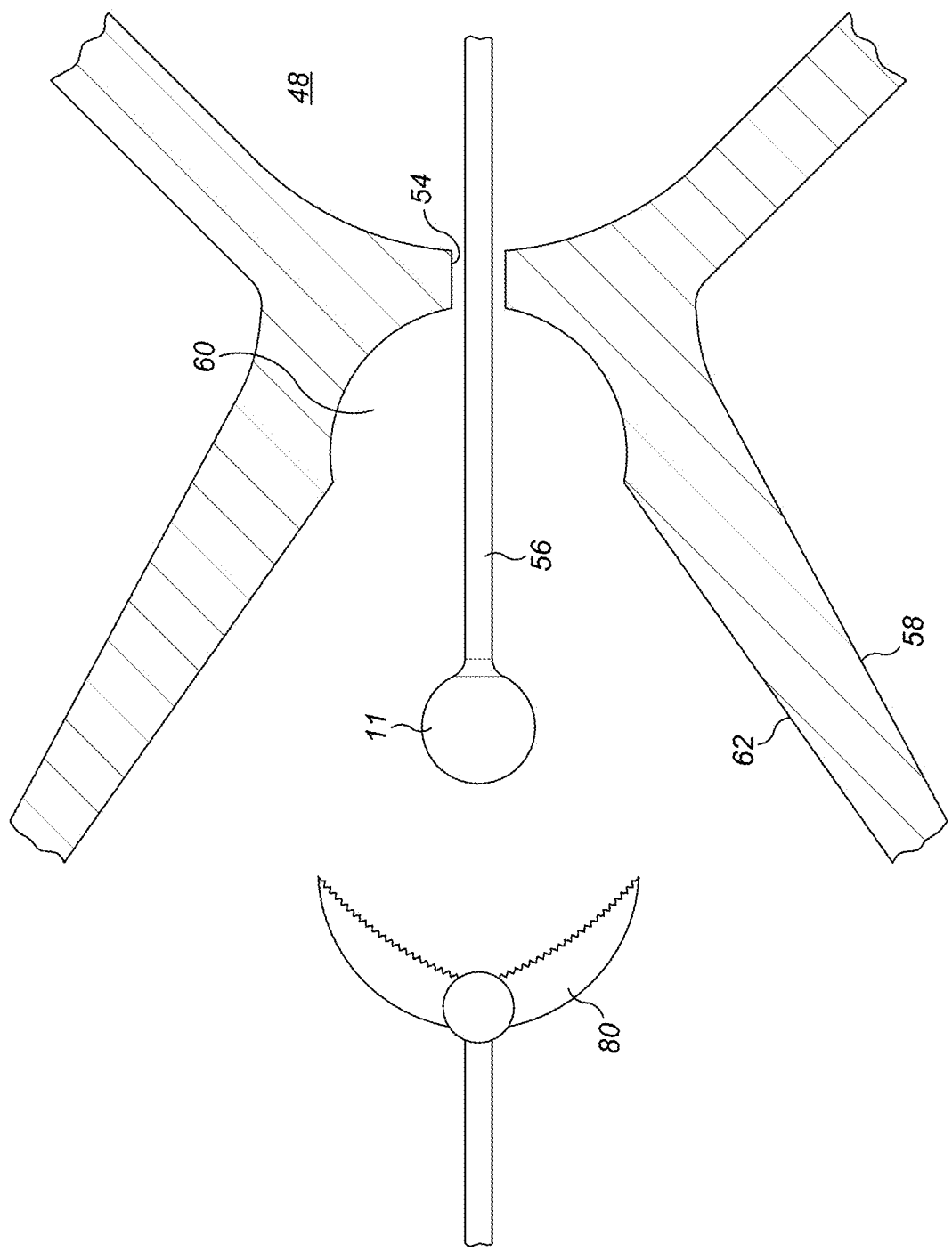

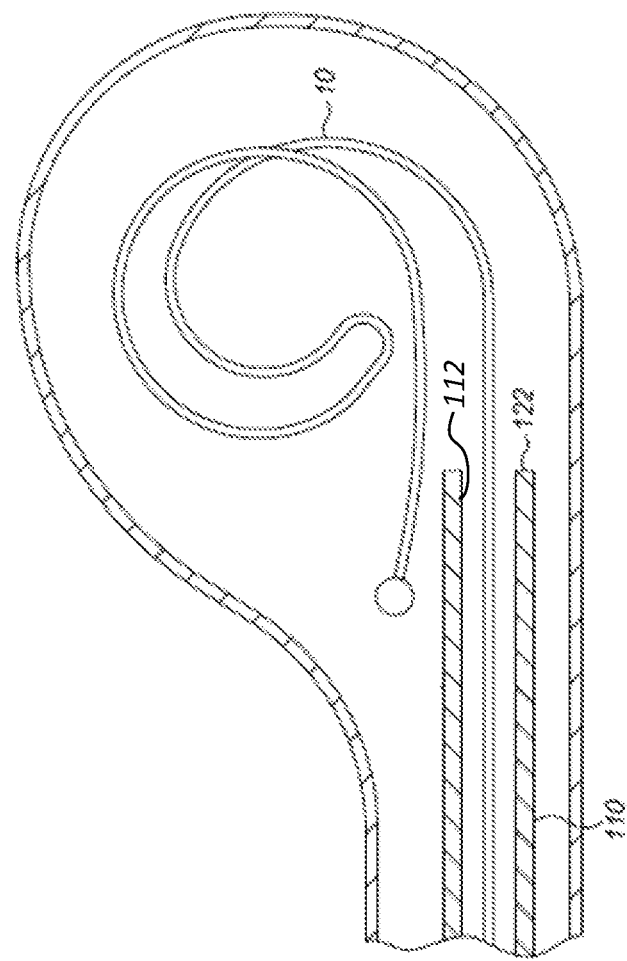

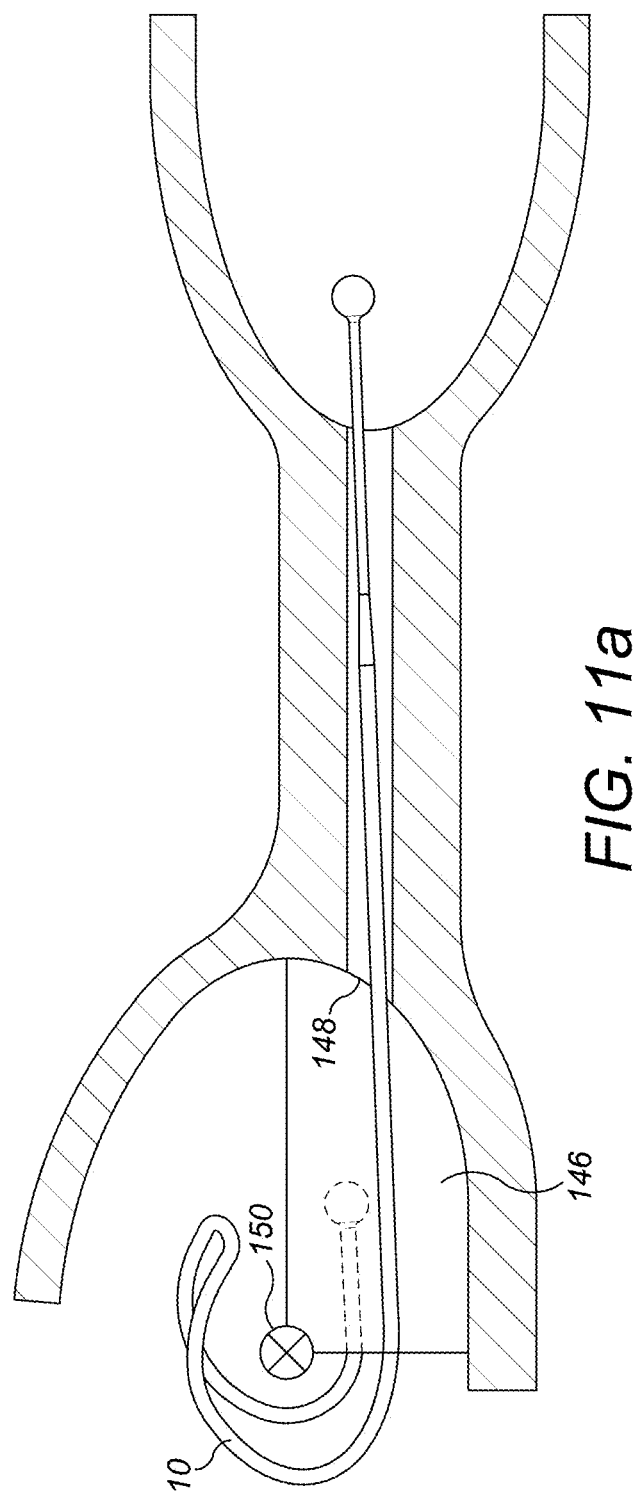

CONTAINERS FOR MEDICAL DEVICES

CROSS REFERENCE TO RELATED APPLICATIONS

The present application claims the benefit of U.S. Provisional Application Ser. No. 62/402,730, filed on Sep. 30, 2016, which is incorporated by reference herein in its entirety for all purposes.

FIELD OF THE INVENTION

The invention relates to improved containers or shell encasings for a medical device, such as an elongate implant that is produced in a predetermined configuration. The invention aims to provide the device with protection from physical damage, prevent snagging of the device during withdrawal or deployment from the container, provide the possibility of sterile handling, and provide a convenient presentation for surgical use.

BACKGROUND OF THE INVENTION

Certain types of medical devices are provided in the form of elongate implants that are deployed in the body and assume a predetermined configuration so as to apply force to internal tissues. One example of such devices is a lung volume reduction coil (LVRC), for example a nitinol wire that is prepared in a coiled configuration, stressed into a relatively straight delivery configuration for delivery into the lung through a catheter, and allowed to resume its compact coiled shape in the lung. Examples of LRVCs and their therapeutic uses can be found in WO2007/106495 and WO2010/030993.

It has been proposed to provide the LVRC in a rigid container to protect the LVRC from handling and damage during shipment, and to provide a relatively sterile packaging in which an LVRC may be shipped unstrained in its original manufactured coiled shape. Where such a container is used, it is necessary to be able to couple the LRVC to a forceps-like device for withdrawing the LRVC form the container into a delivery cartridge. The spring-like nature of the LVRC can make grasping the end of the device, and withdrawing it smoothly from the container difficult in certain cases.

It is against this background that the present invention has been made. Accordingly, improved containers or shell encasings for medical devices, and particularly LVRC are desired.

SUMMARY

The various aspects of the invention relate to improved containers or shell encasings for a medical device, such as lung volume reducing implants (e.g., coils). The container comprises a housing defining a cavity for receiving the device, a coupling zone external to the cavity, and an exit aperture between the cavity and the coupling zone; and a bearing surface located within the cavity, the bearing surface, exit aperture and coupling zone defining an exit path along which the device can be moved for deployment from the container.

In a first aspect of the invention, the bearing surface is spaced from the exit aperture and arranged, together with the coupling zone, such that the exit path is substantially straight.

In a second aspect of the invention, the cavity is approximately cylindrical, and the bearing surface, the exit aperture, and the coupling zone are aligned such that the exit path extends in a direction that is substantially tangential to the cavity.

In a third aspect of the invention, the housing comprises a two part structure joined together in a plane substantially orthogonal to the exit path.

In a fourth aspect of the invention, the housing defines a substantially unobstructed cavity for receiving the device.

In a fifth aspect of the invention, the housing in the coupling zone defines a slot through which the exit path extends, the slot defining a restricted space for deployment of a capture device.

Embodiments of the invention comprise combinations of one or more of the first to fifth aspects of the invention.

The housing can comprise a substantially straight tube structure extending between the cavity and the coupling zone, the tube structure defining the exit aperture, a cavity end of the tube structure being located within the cavity and providing the bearing surface, and a coupling end being positioned at the coupling zone. In this case, the cavity can extend into a region intermediate the cavity end and coupling end of the tube structure.

The housing can comprise a substantially straight tube structure extending in a substantially tangential direction between the cavity and the coupling zone, the tube structure defining the exit aperture, a cavity end of the tube structure being located within the cavity and providing the bearing surface, and a coupling end being positioned at the coupling zone. In this case, the cavity can extend into a region intermediate the cavity end and coupling end of the tube structure.

The housing can comprise a body part and a cap part, wherein the aperture defined when the cap part is separated from the body part provides an inlet opening though which a device can be loaded into the cavity for withdrawal through the exit aperture.

When the housing in the coupling zone defines a slot through which the exit path extends, the slot defining a restricted space for deployment of a capture device, the housing on the side of the slot opposite to the cavity can define a substantially circular section tubular structure, and a transition section between the tubular structure and the slot is provided with smoothly sloping surfaces inner surfaces for directing a capture device so as to be aligned with the slot as it introduced into the coupling zone.

A further aspect of the invention comprises a container according to any of the preceding aspects, further containing a lung volume reduction coil (LVRC) having a proximal portion and a distal portion and having a coiled manufactured shape and a substantially straight delivery shape, wherein the LVRC is in its coiled manufactured shape and the proximal portion lies in the exit path with a proximal end in the coupling zone.

The invention also comprises the use of a container according to any of the preceding aspects for dispensing a lung volume reduction coil.

In one particular aspect, the invention comprises a housing for dispensing a lung volume reduction coil (LVRC), comprising a housing wall with an outer surface and an inner surface, the inner surface defining a cavity suitable for receiving the distal portion of the LVRC in its manufactured shape, the wall having an aperture extending therethrough from the inner surface of the wall to the outer surface of the wall, through which the LVRC may be withdrawn, the proximal end of the LVRC extending through the aperture in use such that the proximal end of the LVRC is accessible from outside the housing; and a guide element having an elongate body with a length defined by a proximal end and a distal end, and a guiding surface along its length, the guiding surface adapted to guide the LVRC between the distal end of the elongate body of the guide element and the aperture; the elongate body extending from a proximal end adjacent the aperture, projecting from the inner surface of the wall adjacent the aperture into the cavity and terminating in a distal end, the guide element being adapted to tension the LVRC into a straightened form as the proximal end of the LVRC is withdrawn from the housing.

The guide element may define a guide path that directs the LVRC to the aperture. Preferably, the housing comprises an outer chamber and an inner chamber, the aperture being shared between and connecting the outer chamber with the inner chamber, the inner chamber comprising the cavity suitable for enclosing the distal end of the LVRC, the outer chamber suitable for receiving the proximal end of the LVRC, the outer chamber having a larger second aperture suitable for receiving open forceps such that the proximal end of the LVRC is accessible with forceps from outside the housing. Although the outer chamber is not necessary, the two-chambered housing is preferable because the outer chamber protects the proximal portion of the LVRC, thus minimizing handling of the LVRC and maintaining relative sterility, while still permitting access to the LVRC with forceps.

The housing or the outer chamber of the housing may comprise a receiving tube for receiving the open forceps, the distal end of the inner surface of which is contiguous with the rim surrounding the aperture.

The guiding surface may be planar or the guiding surface may be concave and contiguous with the rim surrounding the aperture. The guide element may be a tube with an inner surface, outer surface and a lumen, the inner surface of the tube being concave and providing the guiding surface.

The guide element may function both to keep the distal end of the LVRC away from the aperture as the proximal end is guided through the aperture, and also to serve as a pivot point around which the curved distal portion of the LVRC will pivot as it is straightened. Depending on the nature and orientation of the guide element and particularly if the guide element may also serve as a pivot for the distal portion of the LVRC, the housing may contain a spool or may be spoolless.

Preferably, the receiving tube is configured to constrain opened forceps of a delivery device into only two possible orientations/configurations, the first configuration of the forceps being a 180 degree rotation of the second configuration, so that the opened forceps are forced into being centered on and aligned with a ball at the proximal end of the LVRC. Optionally, the inner wall of the receiving tube encloses a lumen which is oblong rectangular or oval in cross-section for receiving the open forceps in one of the two configurations.

The housing may be formed of two sections, each section having a rim, and wherein the rims of the sections do not intersect the rim of the aperture in the housing through which the LVRC may be withdrawn. The rims of the sections may be fitted together in an interference fit.

In a yet further aspect of the invention, in a method of dispensing a lung volume reduction coil, the LVRC may be further tensioned into a straightened form by a receiving tube as the proximal end is withdrawn from the housing, wherein the receiving tube is for receiving open forceps, the distal end of the inner surface of which is contiguous with the rim surrounding the aperture. The LVRC may also be further tensioned into a straightened form by a loading cartridge prior to delivery into the delivery catheter, or may be further tensioned to be delivered from the housing directly to the delivery catheter without first being tensioned into a straightened form by a loading cartridge.

Various changes may be made within the scope of the various aspects of the invention as defined by the claims.

BRIEF DESCRIPTION OF THE DRAWINGS

FIG. 8 shows the proximal end of an LVRC in the device of FIGS. 4a-c in the receiving area of the housing;

FIG. 10 shows a cutaway close-up view of the guide element of the container of FIGS. 9a-b;

FIGS. 11a-b show cutaway close-up views of alternative embodiments of the invention;

DETAILED DESCRIPTION OF THE INVENTION

Figure 1:
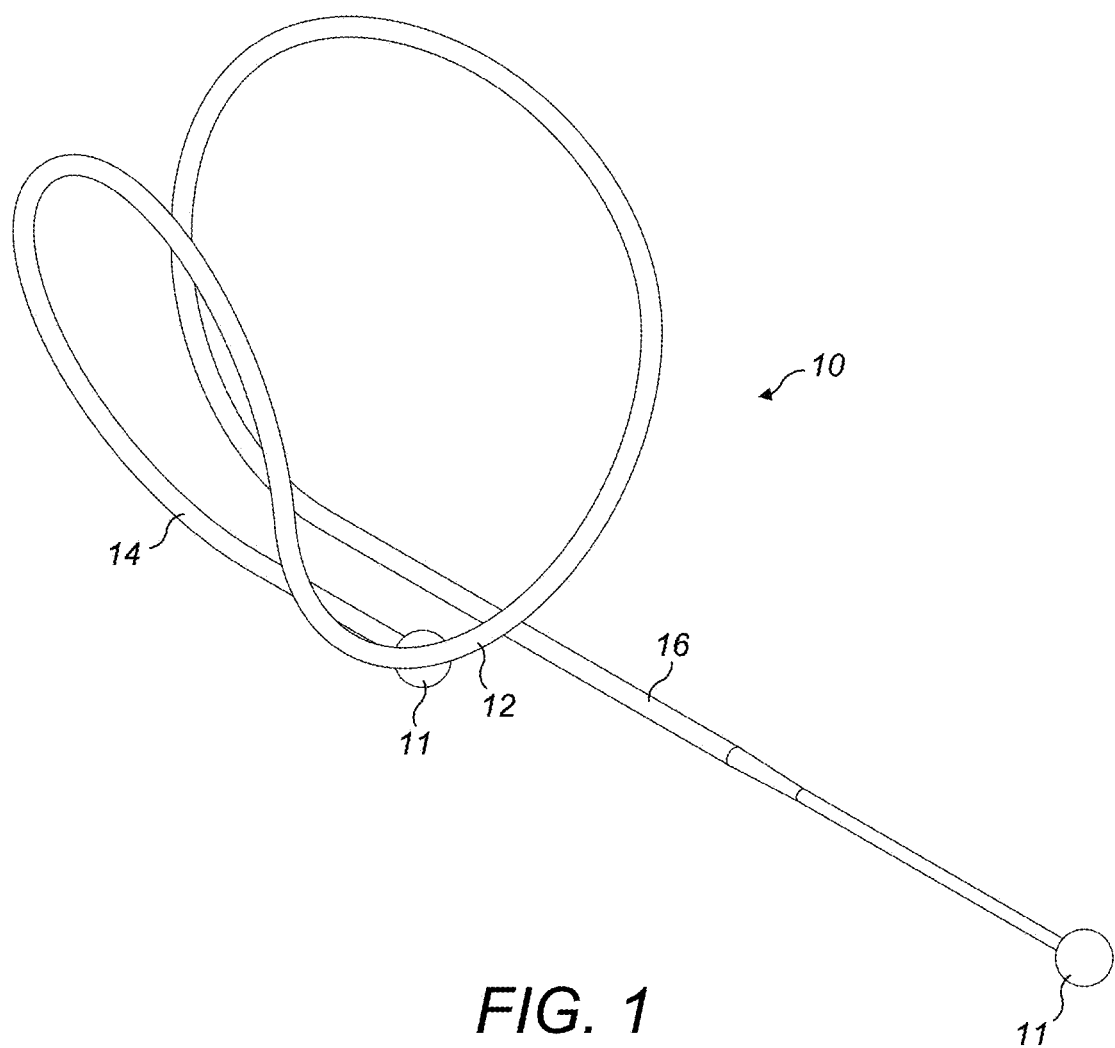
FIG. 1 shows a lung volume reduction coil (LVRC)

FIG. 1 shows a lung volume reduction coil (LVRC). For patients with severe emphysema, treatment with LVRCs is designed to help improve exercise capacity, lung function and quality of life. The LVRC 10 comprises a preformed shape memory coil of a metal such as nitinol, with atraumatic ends 11, typically in the form of ball structures. The preformed shape of the LVRC can be a coil, a baseball seam shape, a saddle-shape, a U-shape having the base of the U curved about an axis parallel to the plane of the U and perpendicular to the axis of the U, a shape that is pre-programmed so that its distal portion approximately circumscribes the volume of a sphere, or (using knot tying terms, see The Ashley Book of Knots, Faber & Faber, $1^{st}$ published 1944, reprinted with amendments 1993, p 13) a shape comprising a closed loop with the central bight 12 looped back so as to lie over the legs 14, 16. Any of these shapes can be used as an alternative to any particular shape mentioned in this document, unless otherwise indicated.

Figure 3:
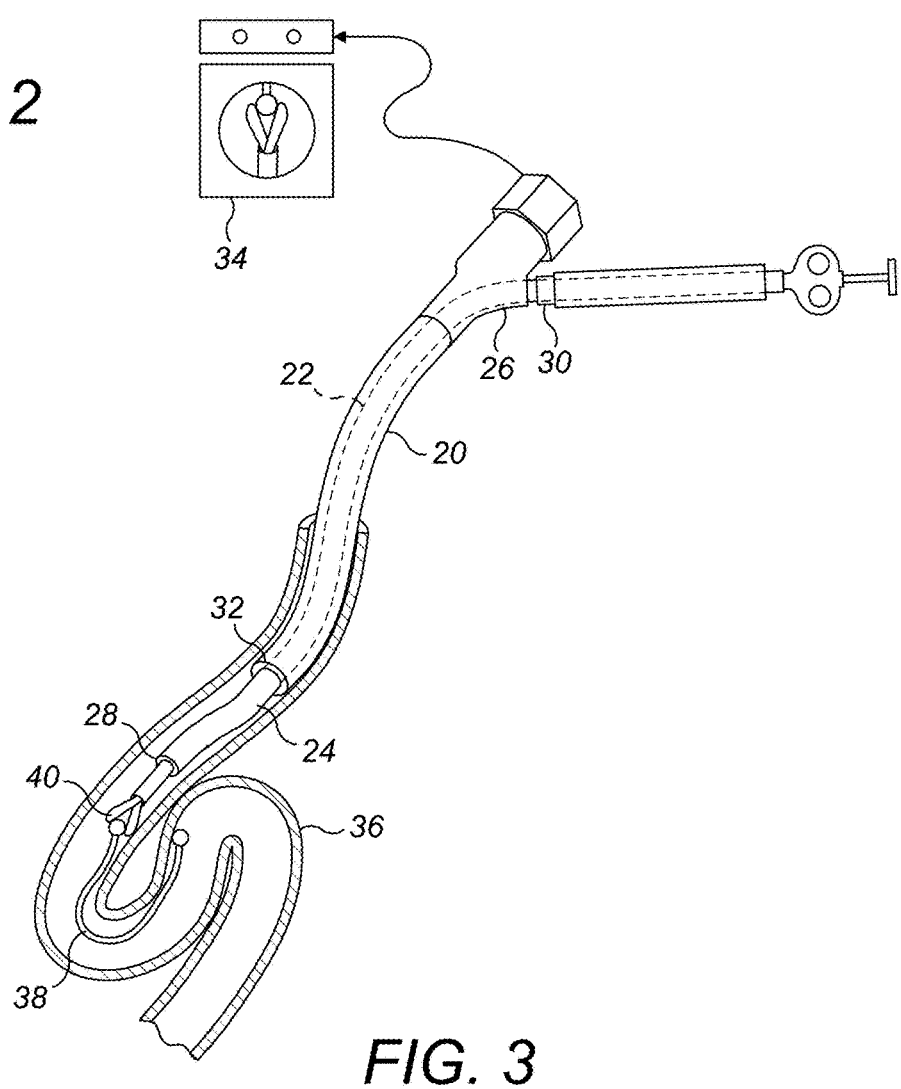
FIG. 3 shows the delivery of an LVRC to a patient's airway.

The LVRC is delivered to a patient's lung in a straightened form using a catheter procedure (FIG. 3). Subsequent recovery of the device to its original manufactured shape when the device is in contact with the inner wall surrounding the lumen of a patient's airway supplies force that urges the patient's airway into a bent, folded or rolled configuration. This effectively shortens the airway structure within the lung. Since the airways are well anchored into lung tissue, the shortened airway provides tension on the surrounding lung tissue. The bending, folding and rolling of the airways resulting from the implantation of LVRCs rolls up diseased tissue and reduces air trapping; the volume of diseased tissue in the lung is thus reduced. By compressing the lung tissue, implantation of one or more LVRCs can result in an increase in elastic recoil and tension in the lung. Additionally, in some instances, lung function can be at least partially restored regardless of the amount of collateral ventilation. Further, the patient's diaphragm may, in some instances, move up once greater tension is created, which enables the lung cavity to operate more effectively. The implantation of LVRCs is described in further detail in WO2007/106495 and WO2010/030993.

Figure 2:
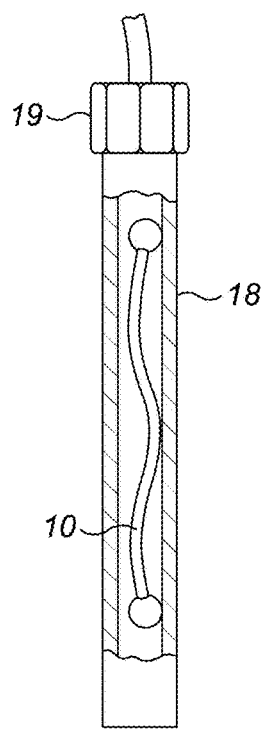
FIG. 2 shows a cutaway view of a delivery cartridge system.

PneumRx, Inc. (Santa Clara, Calif., USA, a BTG international group company) presently manufactures nitinol LVRCs and ships them in their unstrained, original manufactured shape. During preparation for implant, the LVRCs are typically reshaped into a delivery configuration by a cartridge that straightens the LVRC, prior to the LVRC being drawn into a bronchoscope or a catheter for delivery into a patient's lung in a straightened form. Such a cartridge 18 containing an LVRC 10 is shown in FIG. 2. PneumRx™ LVRCs are not shipped in a straightened form, because of the risk of reprogramming a straightened LVRC if it is exposed to heat, i.e. temperatures in excess of approximately 100° C. During manufacture, the nitinol shape memory LVRCs are programmed into their manufactured shape through a heat treating process, which results in coils of a specified strength, the strength being dependent on the manner in which the LVRC is heat processed. In the austenite phase, the nitinol metal recovers to its preprogrammed shape. The temperature at which the nitinol has fully recovered is known as the $A_f$ temperature (austenite final), and typically the strength of a given coil is expressed in terms of its $A_f$ temperature.

PneumRx™ LVRCs are typically produced with an $A_f$ lower than both room and body temperature, so that they are elastic at both room and body temperature and perform as springs at these temperatures. In the straightened or strained form the austenite to martensite phase transition occurs at a much lower temperature than would otherwise occur if the LVRC is unstrained. Were the LVRCs to be shipped in their strained or straightened form, care would need to be taken to ensure that the coils were not heated to temperatures in excess of approximately 100° C. so as to prevent their reprogramming and possible loss of functionality. (In the case of unstrained LVRCs, the temperature is much higher at around 300° C.) Thus, if LVRCs were to be shipped in their straightened form, their packaging would need to indicate that temperatures in excess of approximately 100° C. had not been reached. Manufacturing such packaging would require additional validation and expense.

PneumRx™ LVRCs are typically e-beam sterilized prior to shipment, and although patients are typically receiving prophylactic antibiotics, it is preferable to minimize handling to maintain the relative sterility of the LVRCs prior to and during their implantation, particularly since severe emphysema patients may also be immunocompromised. Presently each LVRC is shipped in a container functioning to maintain the relative sterility of the LVRC and to protect the LVRC from handling and damage during shipment.

The present invention relates to improvements to containers for the LVRC. The container 42 shown in FIGS. 4a-c, comprises a housing wall 46 with an outer surface and an inner surface, the inner surface defining a cavity 48 suitable for enclosing the LVRC 10 in its manufactured shape. The housing further comprises a spool 50 for receiving and holding the preformed curved distal end 52 of the LVRC. This spool provides a bearing surface against and around which the preformed curved distal end pivots as the coil is withdrawn; this provides the necessary tension to straighten the coil so that the coil may be withdrawn through an aperture in the housing. The housing further comprises an exit aperture 54 extending through the housing wall through which the LVRC may be withdrawn, the proximal end 56 of the LVRC extending through the aperture in use such that the proximal end is accessible from outside the housing. The housing further comprises a housing wall with an inner and outer surface surrounding a bell-shaped receiving area 58 for receiving the forceps used to withdraw the LVRC, the bell-shaped receiving area being roughly spherical 60 in the area adjacent the aperture outside the enclosed cavity, and opening into a frustoconical void 62 at a wider end that is more distant to the aperture. In use, the forceps may be inserted into the void for withdrawal of the proximal end of the LVRC. The housing wall surrounding the receiving area protects the LVRC while enabling access to and withdrawal of the proximal end of the LVRC from the housing through the void in the receiving area. In other words, the housing comprises an outer chamber and an inner chamber, the aperture being shared between and connecting the outer chamber with the inner chamber, the inner chamber comprising the cavity suitable for enclosing the distal end of the LVRC, the outer chamber suitable for receiving the proximal end of the LVRC, the outer chamber having a larger second aperture suitable for receiving open forceps such that the proximal end of the LVRC is accessible with forceps from outside the housing.

Figure 4A:
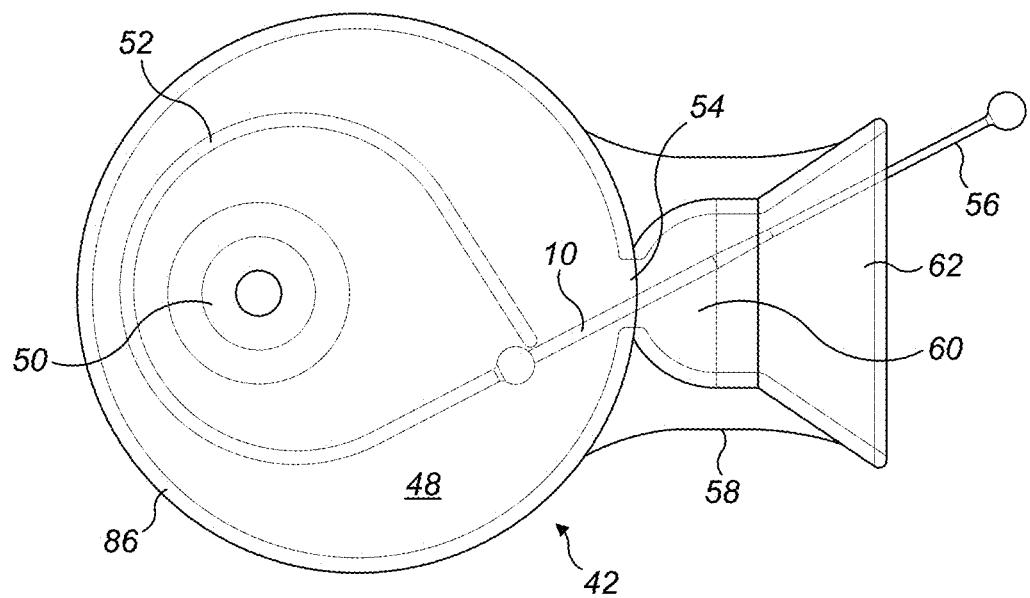
FIGS. 4a-c show a housing for dispensing an LVRC.
Figure 4B:
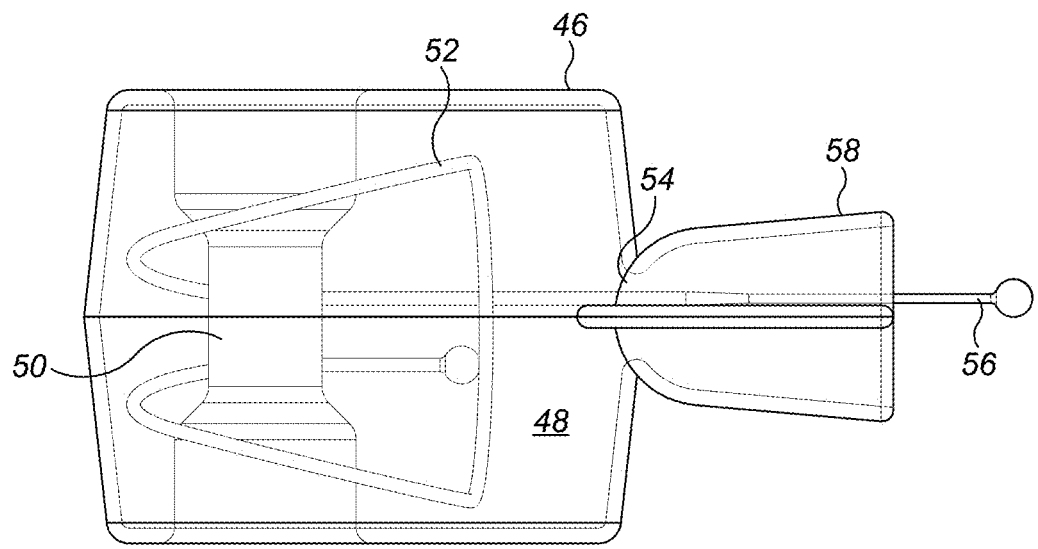
Figure 4C:
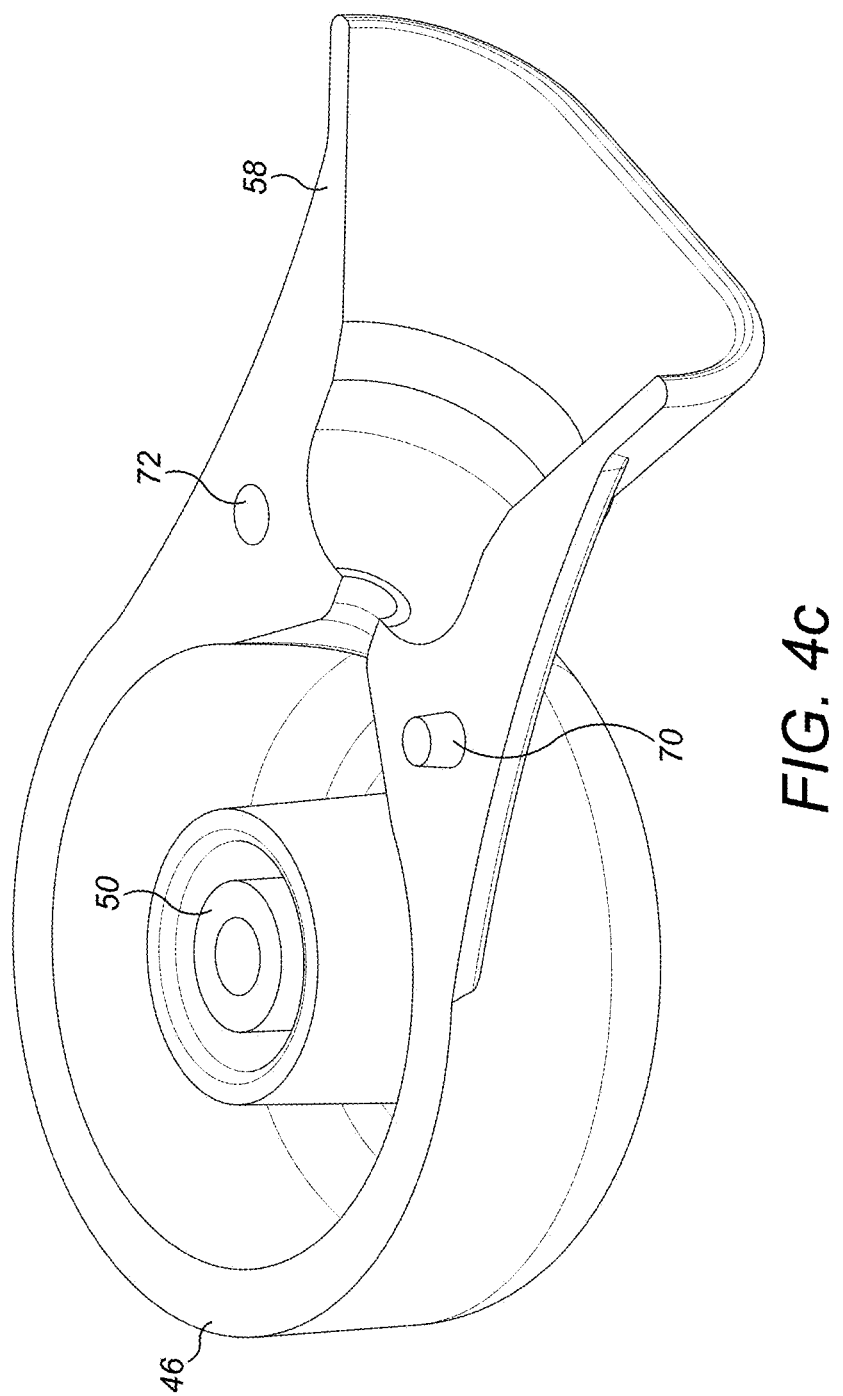

Several shortcomings of the container shown in FIGS. 4a-c involve difficulties faced as a user is withdrawing the LVRC from the housing using forceps. The LVRC may stick or tangle in the housing in various ways as the coil is withdrawn from the housing or the user may have difficulty grasping the proximal end of the LVRC with the forceps within the void in the receiving area. In addition, the housing includes a central spool around which the LVRC is wrapped when loaded into the housing. The LVRC will bear against this spool, as well as the inside wall of the housing as it is withdrawn from the container, the friction arising from this contact impeding smooth withdrawal of the LVRC from the container.

Figure 5:
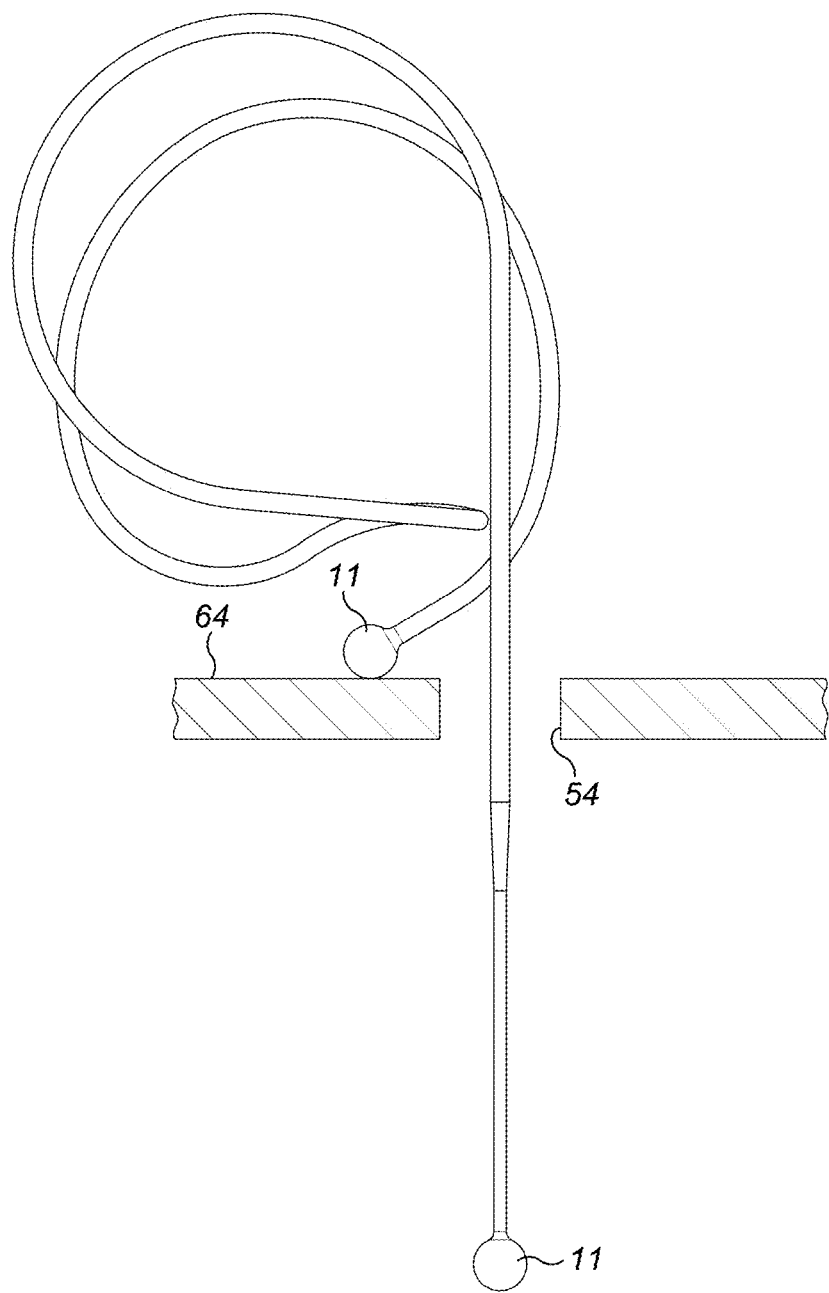
FIG. 5 shows a partial view of the device of FIGS. 4a-c with the distal ball of the LVRC becoming caught and stuck on the inner surface of the wall of the housing.

The proximal and distal ends of the LVRC have balls 11 positioned thereon. When a user withdraws the LVRC through the aperture 54 in the housing, due to the stiffness of the LVRC, in some instances instead of moving freely around the inner surface of the housing wall, the distal ball of the LVRC may become caught and stuck on the inner surface 64 of the wall of the housing adjacent the aperture as shown in FIG. 5. This may result in kinking of the LVRC. The LVRC generally recoils with a snapping motion and the distal end eventually exits the aperture as the user continues to pull the proximal end with the forceps, but there is increased difficulty for the user to withdraw the LVRC from the housing and the user must apply a greater amount of force than if the movement of the LVRC were more smooth.

Figure 6:
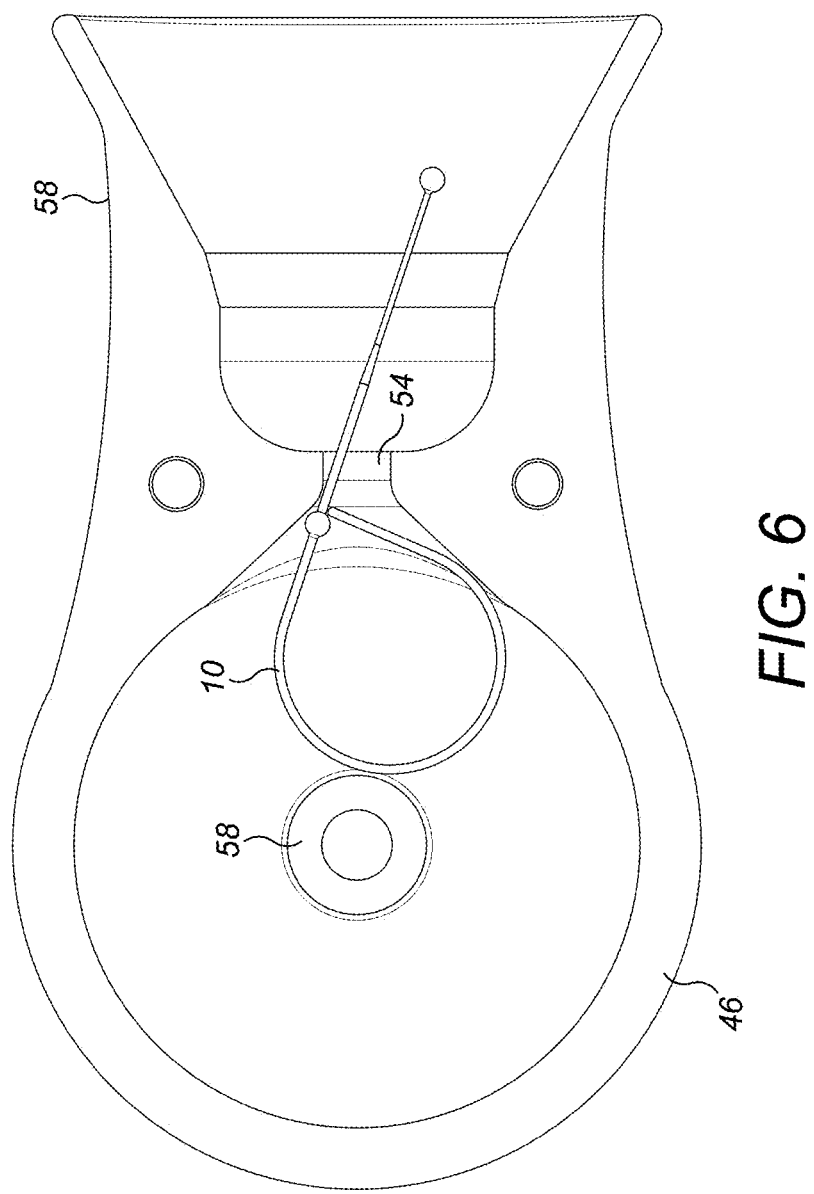
FIG. 6 shows tangling of an LVRC in the device of FIGS. 4a-c on the side of the spool proximal to the user.

Additionally, LVRCs come in several sizes for use in the bronchoscopic procedure. WO2010/030993 relates to selection of an LVRC from a plurality of alternatively selectable LVRCs, wherein the length of the elongate body of the LVRC varies between the LVRCs. This is accomplished using an indexed guidewire extendable distally along the delivery catheter suitable for selecting an LVRC of appropriate length for implantation. When a relatively large guidewire is used (typically being over 5 Fr, such as a 5 ½ Fr guidewire), the cross-section of the guidewire may limit advancement to a region of the airway having a lumen size appropriate for receiving the LVRC. To select an LVRC of appropriate length, the radiopaque indices on the guidewire are counted using fluoroscopy or remote imaging to measure the length of guidewire between the distal end of the guidewire and the distal end of the broncoscope or catheter. Usually in a procedure, one individual in a surgical team measures a patient's airway while another technician selects an LVRC of appropriate length and prepares it for implantation by using forceps to draw the LVRC into a cartridge for straightening. The technician typically hands the forceps/coil/cartridge system to the physician—the Luer lock on the cartridge is fitted to that on the catheter, and then the straightened coil is pushed out into the catheter for delivery—the catheter at this point is already in the patients lung, guidewire has been removed after the airway has been measured. Each LVRC, if or when selected, can be loaded into the catheter by straightening the associated elongate body toward the axis and inserting the elongate body into the lumen so that the catheter maintains the elongate body in the delivery configuration. Occasionally, the measurement of the patient's airway is different than expected, an inappropriate LVRC is chosen to be drawn from the housing into a cartridge prematurely, or the physician changes his or her mind regarding which length of LVRC to use. With the housing of FIGS. 4*a-c*, if an LVRC is partially withdrawn from the aperture beyond a certain point and then released, the LVRC will fail to pass over the spool and recover its shape in front of the spool. The LVRC may then no longer be usable, as it will be difficult to adequately tension the LVRC for efficient withdrawal of the LVRC from the housing for straightening in the cartridge and catheter. This is shown in FIG. 6.

Figure 7A:
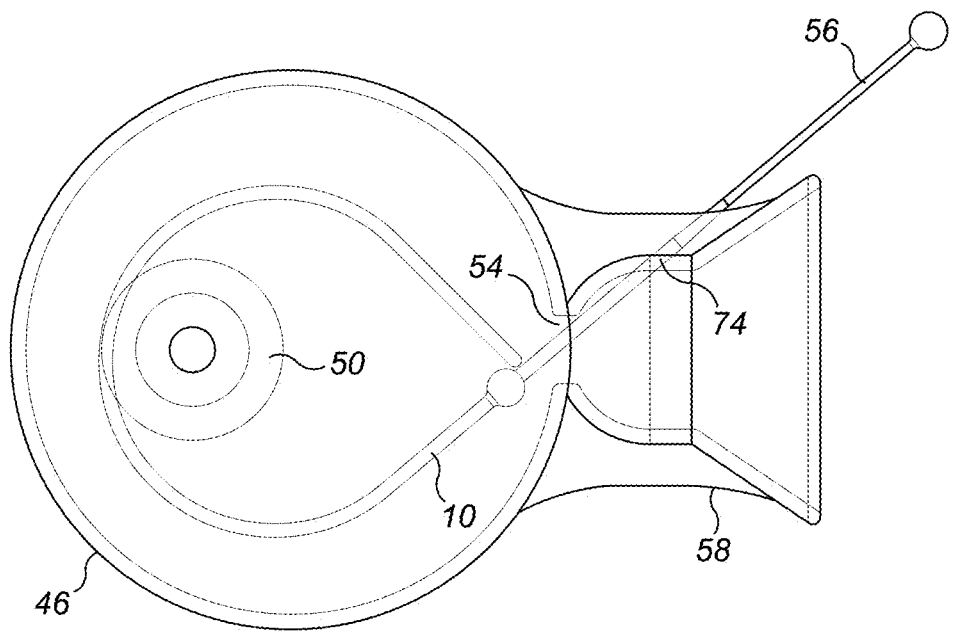
FIGS. 7a-b show sticking of an LVRC in the device of FIGS. 4a-c between rims of sections of the housing.
Figure 7B:
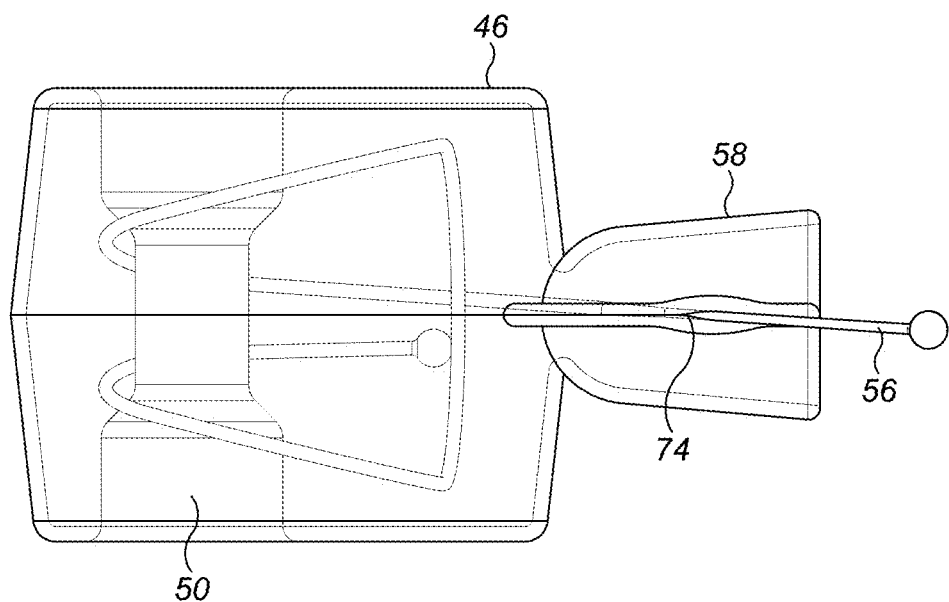

The container of FIGS. 4*a-c* is made from two injection molded halves of polycarbonate plastic, one of which is shown in FIG. 4*c*. The external surface of the housing, the internal surface of which forms the spool portion 50, contains threading for a screw such that a screw may be used to hold the halves together; additionally locating dowels 70 and bores 72 are provided in the matching surfaces of the two halves, which fit together to keep the halves held stably in position. However, occasionally as the LVRC is withdrawn through the aperture 54 between the inner and outer chambers, the LVRC may become stuck in the joint 74 between the halves of the housing, as is shown in FIGS. 7*a-b*. Also, the fact that the proximal end of the LVRC exits the cavity at an angle and so must be bent around the edge of the exit aperture for it to be withdrawn in the correct direction for loading into the cartridge means that the LVRC tends to be dragged into the joint.

The container of FIGS. 4*a-c* comprises an inner chamber and an outer chamber with an exit aperture connecting the inner chamber with the outer chamber. The inner chamber of the housing comprises the cavity suitable for enclosing the distal end of the LVRC, the outer chamber is suitable for receiving the proximal end of the LVRC. The outer chamber has a larger second aperture suitable for receiving open forceps such that the proximal end of the LVRC is accessible with forceps from outside the housing. In the container of FIGS. 4*a-c*, the outer chamber defines an exit path comprising a bell-shaped receiving or coupling area for receiving the forceps 80, the bell-shaped receiving zone 58 being roughly spherical in shape 60 and opening into a wider, second region having a substantially frustoconical section 62, as shown in FIG. 8. In use, the receiving/coupling zone and the second region are relatively large compared to the ball 11 at the proximal end 56 of the LVRC, and it may take a technician or physician several attempts to grasp the ball at the proximal end of the LVRC with forceps.

FIG. 1 shows an LVRC 10 suitable for use with the containers of the invention. The LVRC is shown in its manufactured, coiled shape. The LVRC comprises a shape memory nitinol wire with balls 11 positioned thereon to form the proximal and distal atraumatic ends of the LVRC device. In its manufactured shape, the shape memory nitinol wire is preprogrammed so that its distal portion roughly circumscribes the volume of a sphere; in use after implantation the distal portion of the LVRC gathers and rolls up diseased lung tissue into a roughly spherical volume. The preprogrammed shape of the wire at the distal end may also be described as the contour of a baseball seam or a saddle. The LVRC also has a straight proximal portion which remains straight after implantation, and around which, in use in the lung, lung tissue is not rolled, thus facilitating recapture and removal or in situ adjustment of the LVRC if necessary. The individual LVRC implants may vary in length from one to another and have any suitable length for treating target lung tissue. The LVRC may have a length of over 70 mm, often having a length in a range from about 120 mm to about 250 mm. LVRCs are currently available in lengths of 200, 175, 150, 125, 100, 85, 70 mm. The diameter of the nitinol wire of the LVRC is typically from 0.2 to 0.7 mm, preferably 0.3 to 0.5 mm. The atraumatic proximal and distal balls minimize scraping or gouging of the lung tissue and facilitate manipulation of the LVRC with the forceps for implantation as well as for recapture, removal or in situ adjustment of the LVRC if necessary. The atraumatic proximal and distal balls may typically be formed by melting back a portion of the nitinol wire, and typically have a cross-sectional diameter between 1 and 3 mm, preferably 1 mm.

FIG. 2 illustrates a cutaway view of a delivery cartridge system 18 that constrains the LVRC 10 in a deliverable shape. The cartridge may be used as a tool to more easily load the implant into a desired shape before being installed into the bronchoscope or a catheter delivery device and into the patient. The cartridge may be terminated with open ends or one or more hubs such as the Luer lock hub 19 that is shown. If a Luer lock hub is present it may be used to connect the cartridge to the bronchoscope or catheter delivery device so that the LVRC may be more easily advanced from the cartridge into the bronchoscope or catheter delivery device.

FIG. 3 illustrates a delivery system that may be used to deliver the implant device into the human lung. The many components of the system may be needed to guide the bronchoscope 20 to a site that is appropriate for implant delivery. The catheter 22 is designed to constrain the device in a deliverable shape while it is advanced through the system and into the patient. The distal end 24 may be configured from a floppier polymer or braid than the proximal end 26 and the distal tip 28 may further include a radiopaque material associated with the tip, either integral or adjacent, to identify the position of the tip. Providing one or more radiopaque markers facilitates using x-ray guidance system to position the distal end of the device in situ relative to a target anatomy. The proximal termination of the delivery catheter may further be adapted to incorporate a lockable hub to secure the loading cartridge with a smooth continuous lumen. The delivery catheter 22 is shown introduced into the bronchoscope side port 30 and out from the distal end 32 of the scope. A camera is shown attached to the end of the scope with a cable to transmit the image signal to a processor and monitor 34. The monitor shows a typical visual orientation on the screen of a delivery catheter image just ahead of the optical element in the scope. The distal end 24 of the delivery catheter 22 protrudes out of the scope 20 in an airway 36 where the user will place an implant device 38. The implant is loaded into a loading cartridge that is coupled to the proximal end of the delivery catheter via locking hub connection. A pusher grasper device 40 is coupled to the proximal end of the implant with a grasper coupler that is locked to the implant using an actuation plunger, handle and pull wire that runs through the central lumen in the pusher catheter. By releasably coupling the pusher to the implant device, the user may advance the implant to a position in the lung in a deployed configuration. The user can survey the implant placement position and still be able to retrieve the implant back into the delivery catheter, with ease, if the delivery position is less than ideal. The implant and pusher has been advanced through the delivery catheter to a location distal to the scope into the airway. The pusher grasping jaws are still locked onto the proximal end of the implant but the implant has recovered to a pre-programmed shape that has also bent the airway into a folded configuration. By folding the airway, the airway structure has been effectively shortened within the lung. Since the airways are well anchored into the lung tissue, the airway provides tension on the surrounding lung tissue which is graphically depicted by showing the pulled (curved inward) floor of the lung. The image from the camera is transmitted through the signal processor to the monitor to show the distal tip of the delivery catheter, distal grasper of the pusher and proximal end of the implant. Alternatively, when the distal end of the delivery catheter is beyond the field of view of the camera, a fluoroscopic guidance system may be used. The grasper may be used to locate, couple to and retrieve devices that have been released in the patient. It is easy to envision how the implant performs work on the airways and lung tissue without blocking the entire lumen of the airway. This is a benefit in that fluid or air may pass either way through the airway past the implant device.

FIGS. 9 a-b show an embodiment of the container 100 of the present invention. The container may be made of any suitable material, but is typically made of polycarbonate plastic. The container defines a housing of a size suitable for dispensing an individual LVRC 10. The individual LVRCs come in various sizes; typically the various sizes for the housing may be approximately 5 to 7 cm in length, approximately 1 to 2 cm in width at their widest points, and approximately 1 to 2 cm in height at their highest points. The container comprises a housing wall 104 with an outer surface and an inner surface, the inner surface defining a cavity 102 suitable for enclosing the distal end portion of the LVRC in its manufactured shape, the wall having an exit aperture 106 extending through which the LVRC may be withdrawn, the proximal end of the LVRC extending through the aperture in use such that the proximal end is in a coupling zone 108 external to the cavity and is accessible from outside the housing. The housing further comprises a guide element 110 having a guiding/bearing surface 112 extending from the inner surface of the wall adjacent the exit aperture and projecting into the cavity, the guide element/bearing surface being adapted to tension the LVRC into a straightened form as the proximal end is withdrawn from the housing. This guide element is in the form of a tube structure 114, which projects from the inner surface of the wall adjacent the aperture into the cavity of the housing. The inner wall of the tube forms a concave guiding surface which guides the LVRC to the exit aperture through which it may be withdrawn. The housing shown comprises an outer chamber (coupling zone) 108 and an inner chamber (cavity) 102, the exit aperture 106 connecting the outer chamber with the inner chamber. The inner chamber comprises the cavity suitable for enclosing the distal end portion of the LVRC, the outer chamber comprises the coupling zone suitable for receiving the proximal end portion of the LVRC. The outer chamber has a larger second aperture 116 suitable for receiving open forceps such that the proximal end of the LVRC is accessible with forceps from outside the housing. The outer chamber shown further comprises a receiving tube 118 for receiving the open forceps, the distal end of the inner surface of which is contiguous with the rim surrounding the exit aperture. In the embodiment shown, both the receiving tube for receiving the forceps and the guide element tube are contiguous with the rim surrounding the aperture. As will be appreciated, the exit path formed by the guiding/bearing surface 112, exit aperture 106, and coupling zone 108 extends in a substantially straight tangential direction with respect to the approximately cylindrical cavity 102. Thus the distal portion of the LVRC is left free to rotate in the cylinder-like cavity as the LVRC is progressively fed through the tube. In addition, the LVRC does not need to be further distorted once it has passed through the exit aperture before it is loaded in to a cartridge.

Figure 9A:
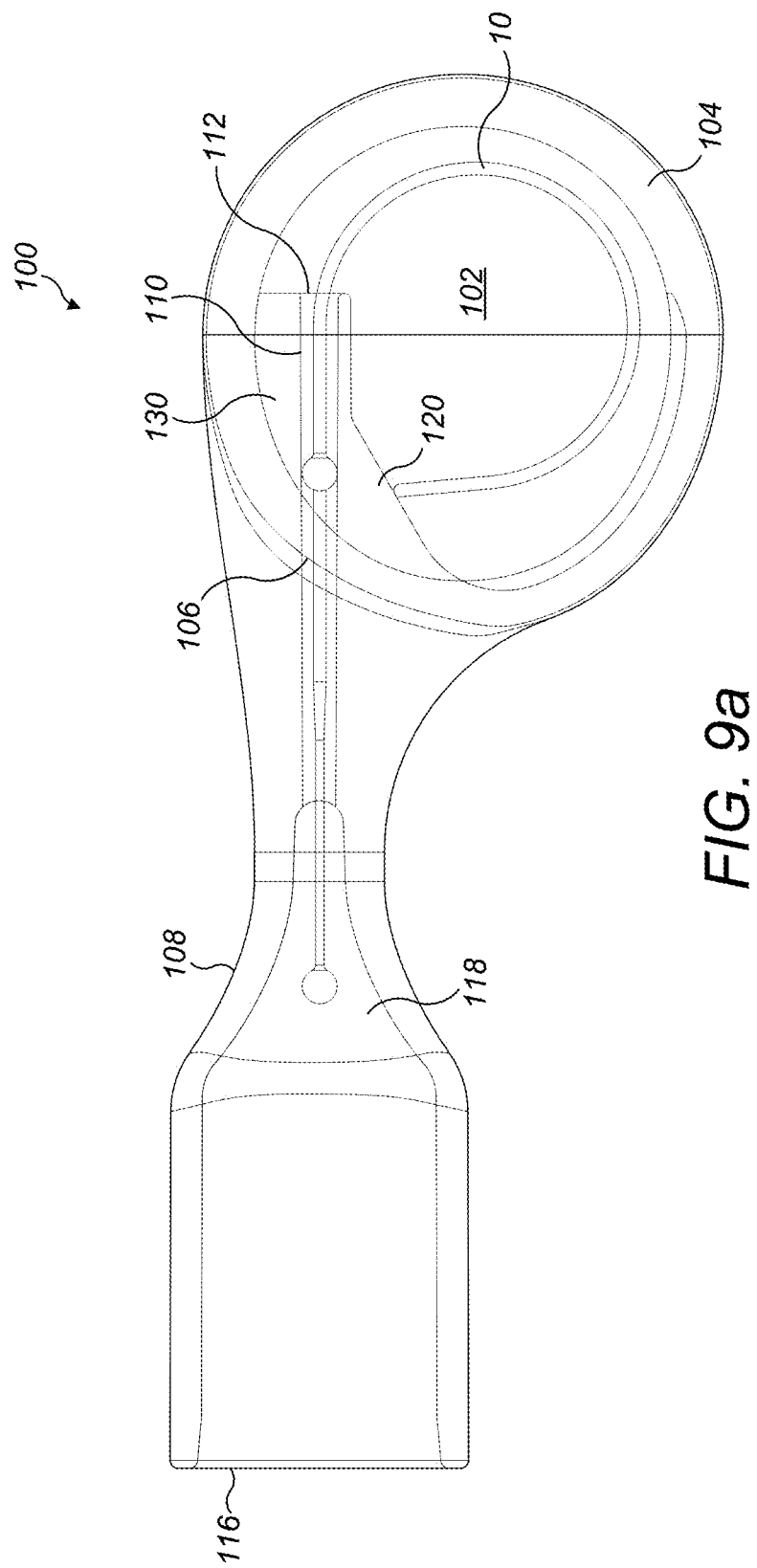
FIGS. 9a-b show an embodiment of the container of the present invention.

The shape of the housing generally corresponds to the shape of the LVRC and only has one mirror axis of symmetry as opposed to two in the container of FIG. 4. It thereby minimises plastic use. The shape of the housing in FIG. 9a also avoids difficulties encountered in tensioning the coil if the chamber is tilted in use by the physician or assistant. When the chamber of FIG. 4 is tilted, the LVRC is able to move freely within the chamber 48 in the direction of the tilt, which exacerbates difficulties tensioning the LVRC as discussed with reference to FIG. 5. In FIG. 9a, because outer chamber 108 is tangentially offset from chamber 102 and chamber 102 is appropriately sized for the LVRC, i.e., not so small that the LVRC rubs against the inner surface as it is withdrawn nor so large that the LVRC moves freely within chamber 102, and because the distal portion of the LVRC is constrained within guide element 110, this difficulty when the housing is tilted in use is avoided. One piece 120 connects the guide tube to the inner surface of the wall of the housing and abuts the distal portion of the coil, the distal portion of the coil sliding against it as it is withdrawn. Piece 120 also prevents the coil from jamming against the inner surface of the housing as the coil is withdrawn. The other piece 130 keeps the distal end of the coil from becoming stuck between the tube and the housing as it is withdrawn.

Figure 9B:
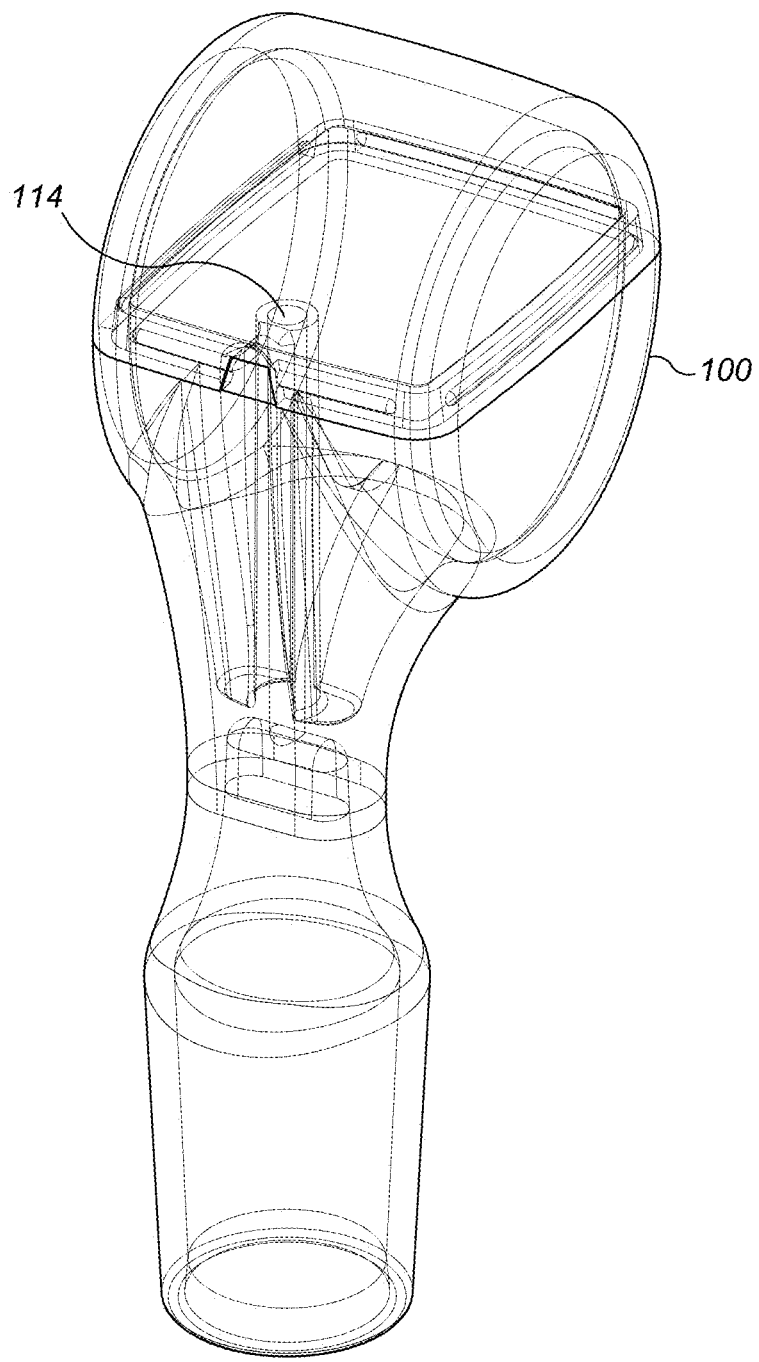

FIG. 10 shows a cutaway close-up view of the guide element of FIGS. 9a-b. This guide element is in the form of a tube 110, which projects from the inner surface of the wall adjacent the exit aperture into the cavity 102 of the housing. The inner surface 112 of the wall of the tube forms a guiding/bearing surface which guides the LVRC 10 to the exit aperture through which it may be withdrawn. The guide element separates the proximal and distal ends of the LVRC from one another as the proximal end is pulled away from the aperture and out of the housing, keeping the distal end of the LVRC away from the aperture as the proximal end is guided through the aperture. That is to say, the proximal portion of the LVRC is initially inside the lumen of the tube while the distal end of the LVRC is adjacent to the outer surface of the tube before the LVRC is withdrawn. As the LVRC is withdrawn, the distal end of the LVRC is eventually pulled inside the lumen of the tube—this occurs after the proximal portion of the LVRC has been withdrawn from and has exited the housing. Thus the problem shown in FIG. 5, in which the distal ball becomes caught on the inner surface of the wall of the housing adjacent the aperture resulting in kinking of the LVRC and increased difficulty in withdrawal, is avoided, and the LVRC may be withdrawn from the housing in a motion that is more smooth and continuous.

Referring again to FIG. 10, the distal end 122 of the upper inner surface of the wall of the tube provides a bearing pivot point around which the curved distal end of the LVRC may pivot as it is withdrawn from the housing; this provides the necessary tension to straighten the LVRC so that the LVRC may be withdrawn through the exit aperture in the housing. Thus the housing may of the invention may be spoolless or otherwise unobstructed, as shown. If an inappropriate LVRC is chosen or if the physician changes his or her mind regarding which length of LVRC to use, an LVRC that is partially withdrawn from the aperture and then released will be guided by the guide element (in this case, the inner surface of the wall of the tubular guide element) back into the housing as it recovers its original manufactured shape. The LVRC will still be usable following its release back into the housing, as it will again be possible to adequately tension the LVRC for efficient withdrawal from the housing. Additionally, in the case of a spoolless housing, as shown, the LVRC will not be stuck in front of a spool. Thus, the problem shown in FIG. 6 will be avoided.

Figure 11B:
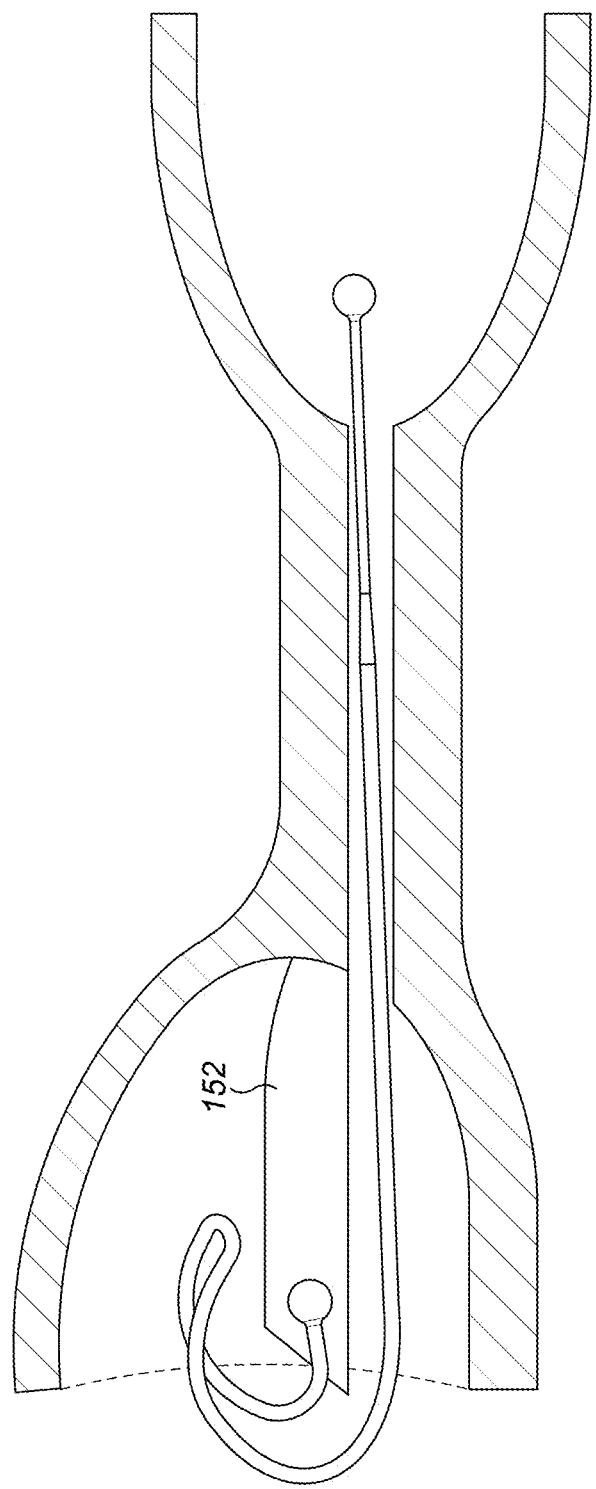

FIG. 11a shows schematically an alternative embodiment of the present invention wherein the guide element 146 has two opposing planar surfaces. The guide element separates the proximal and distal ends of the LVRC from one another as the proximal end is pulled away from the aperture and out of the housing, keeping the distal end of the LVRC away from the aperture as the proximal end is guided through the aperture 148. The proximal portion of the LVRC is shown in front of the guide element, while the distal end of the LVRC is shown behind the guide element. As the LVRC is withdrawn, the distal end of the LVRC is eventually pulled in front of the guide element—this occurs after the proximal portion of the LVRC has been withdrawn from and has exited the housing. Thus the problem shown in FIG. 5, in which the distal ball becomes caught on the inner surface of the wall of the housing adjacent the aperture resulting in kinking of the LVRC and increased difficulty in withdrawal, is avoided. When the guide element is a planar element in a substantially vertical orientation, relative to the rest of the housing, in use, shown in FIG. 11a, the housing can contain a spool 150 as shown. This spool provides a bearing surface against and around which the preformed curved distal end pivots as the LVRC is withdrawn; as the user pulls the proximal end of the LVRC the spool this provides tension to straighten the coil so that the coil may be withdrawn through the aperture in the housing. FIG. 11b shows a guide element that is a planar element 152 in a substantially horizontal orientation, relative to the rest of the housing, in use. The distal end of this guide element provides a single pivot point around which the LVRC may pivot as it is withdrawn. In alternative substantially vertical and substantially horizontal embodiments, instead of a planar surfaces as shown the guide element may have a concave surface.

Figure 12:
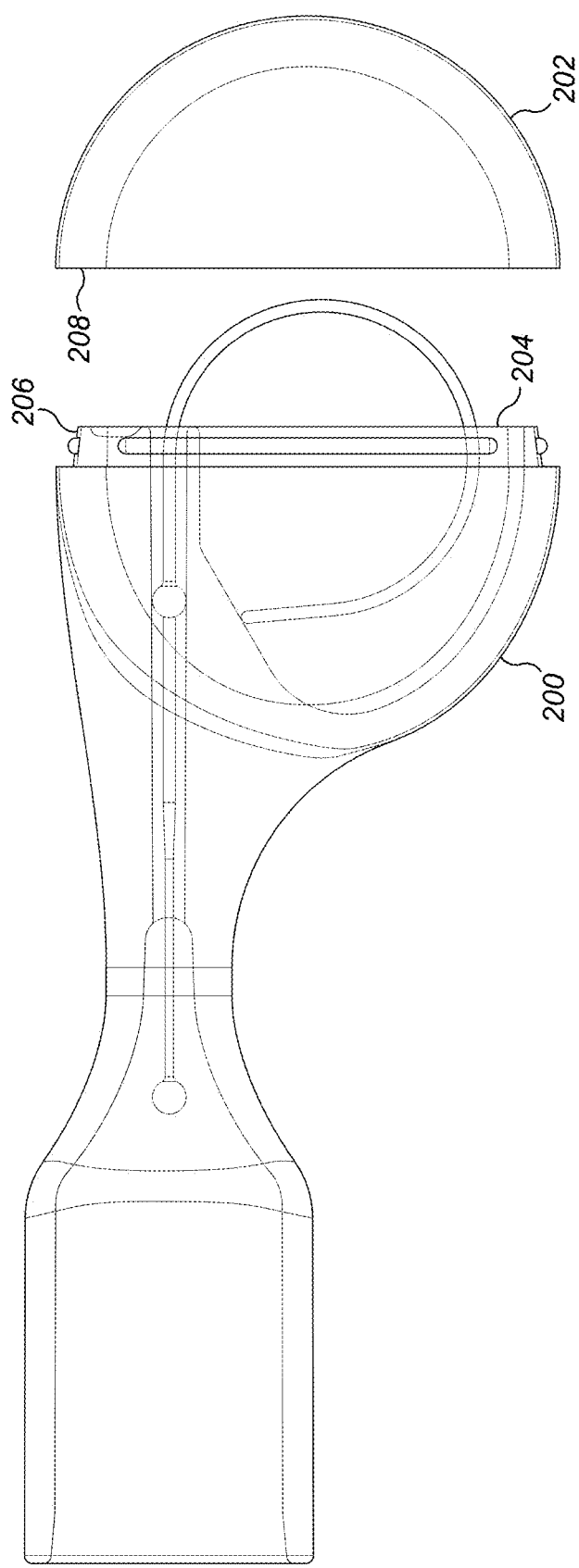
FIG. 12 shows an embodiment comprising a two part construction for a container the of the invention.

FIG. 12 shows an embodiment of the invention comprising a two-part structure having an interference or press fit by which two sections of the housing of the present invention may be snapped together. The two parts comprise a body part 200, defining the main part of the cavity, and a cap part 202. When the cap part is removed from the body part, it provides an inlet or loading aperture 204 through which the LVRC can be loaded into the container. Protrusions 206 on the rim of one section of the housing are met with corresponding indentations 208 on the rim of other section of the housing, and the sections are snap-fitted and held together with friction. The problem of FIGS. 7a-b is thereby avoided for two reasons. Firstly, the interference fit of the two sections forms a tight junction, there is therefore no space or gap as in FIGS. 7a-b into which the LVRC is able to fit to become stuck. Secondly, because the rims of the sections lie in a plane that is orthogonal to the exit path of the LVRC, they do not intersect the rim of the exit aperture in the housing through which the LVRC may be withdrawn, nor do the rims of the sections intersect the perimeter of the receiving tube. Therefore the LVRC will not become stuck between the two sections of housing as it is pulled through the aperture and withdrawn from the housing. Preferably, the two sections of housing may be joined at the widest portion of the cavity, so that the LVRC may be easily loaded into the housing following its manufacture.

Figure 13A:
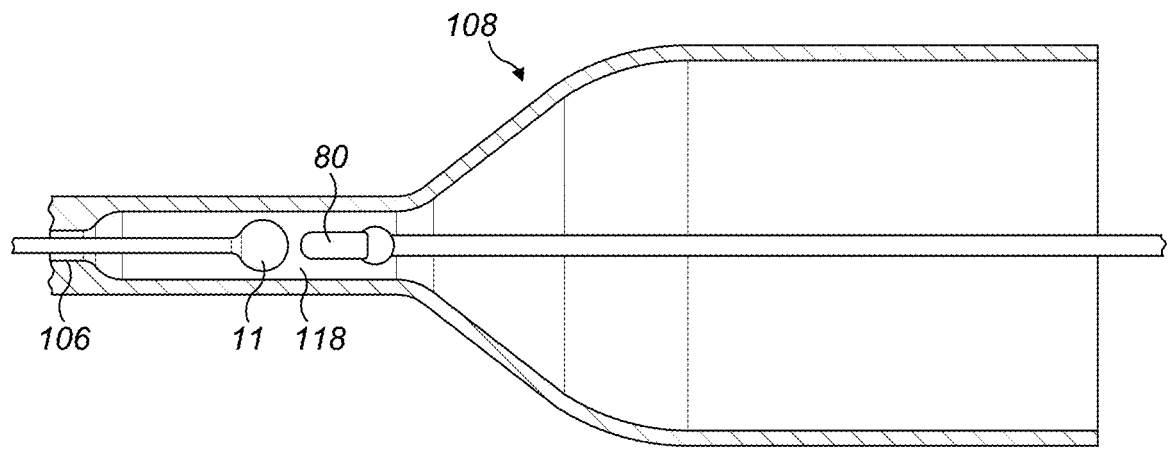
FIGS. 13a-c show the proximal end of an LVRC in the coupling zone of an embodiment of the invention.
Figure 13B:
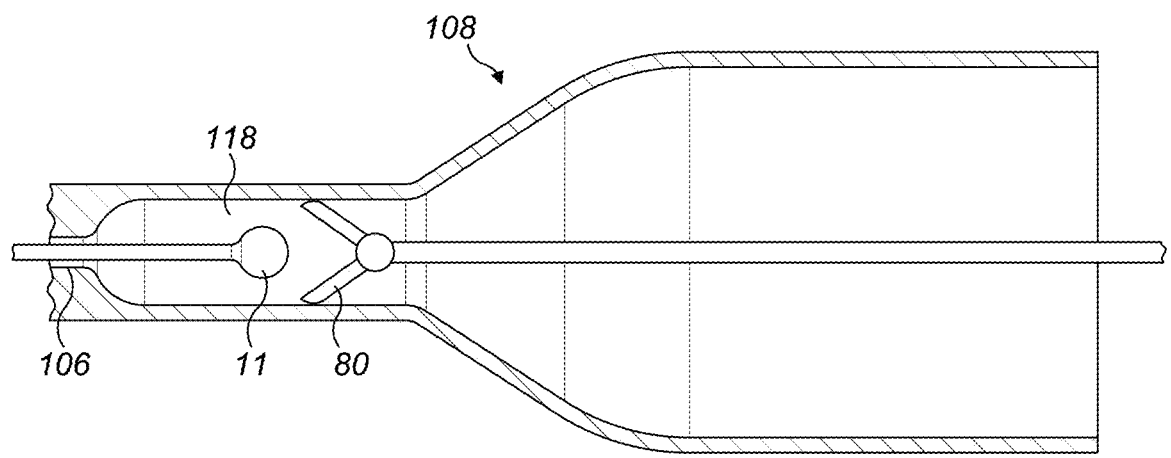
Figure 13C:
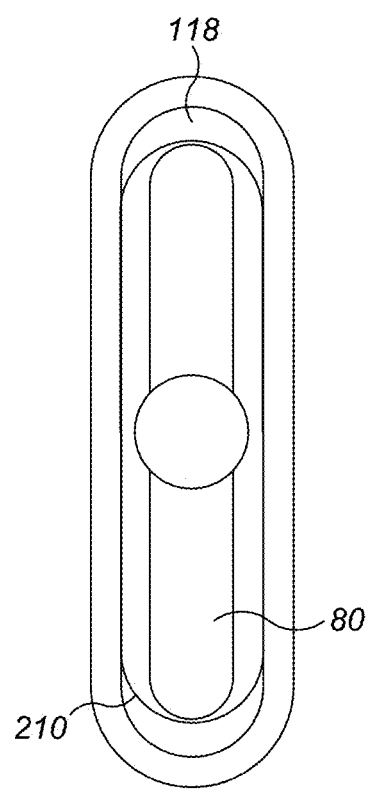

FIGS. 13a-c shows a cutaway view of the outer chamber/coupling zone 108 of the embodiment of FIGS. 9a-b in two perpendicular orientations, along the width and along the depth of the housing. The outer chamber shown further comprises a receiving tube 118 for receiving the open forceps 80, the distal end of the inner surface of which is contiguous with the rim surrounding the exit aperture 106. In the embodiment shown, both the receiving tube for receiving the forceps and the guide element tube are contiguous with the rim surrounding the aperture. The receiving tube is configured as a slot 210 to constrain opened forceps 80 of a delivery device into only two possible orientations/configurations, the one configuration of the forceps being a 180 degree rotation of the other configuration, so that the opened forceps are forced into being centered on and aligned with the ball at the proximal end of the LVRC. Because the opened forceps are forced into one of two configurations, and because the proximal ball 11 is centered in the receiving tube by the tubular guide element it is ensured that the ball at the proximal end of the LVRC will be grasped with the center of the open forceps. Thus, the problem discussed with reference to FIG. 8, in which it may take a technician several attempts to grasp the proximal ball of the LVRC has been avoided, and the proximal ball of the LVRC may even be grasped with the forceps blindly. Additionally, as shown, preferably the lumen of the receiving tube tapers smoothly from a broad diameter tube to a narrower diameter slot so as to guide the forceps to the proximal ball of the LVRC.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

In the previous description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

The invention claimed is:

1. A container for a elongate implant, comprising: a housing defining a cavity for receiving a device, a coupling zone external to the cavity, and an exit aperture between the cavity and the coupling zone; and a substantially straight tubular structure that extends at least partially into the cavity, wherein an inner surface of the tubular structure provides a bearing surface for applying a force to straighten the device, and wherein the tubular structure, the exit aperture, and the coupling zone define an exit path along which the device can be moved for deployment from the container; wherein the tubular structure, the exit aperture, and the coupling zone are arranged, such that the exit path defined by the tubular structure, the exit aperture, and the coupling zone is substantially straight.

2. The container as claimed in claim 1, wherein the tubular structure comprises an elongate body with a length defined by a cavity end and a coupling end, wherein the cavity end terminates within the cavity and the coupling end terminates at the coupling zone, and wherein the tubular structure defines the exit aperture.

3. The container as claimed in claim 2, wherein the cavity end is configured to receive a proximal portion of the device.

4. The container as claimed in claim 1, wherein the cavity is configured to receive a device comprising a lung volume reduction coil (LVRC) having a proximal portion and a distal portion and having a coiled manufactured shape and a substantially straight delivery shape, wherein the housing comprises a housing wall with an outer surface and an inner surface, the inner surface of the housing wall defining the cavity suitable for receiving at least a distal portion of the LVRC in its manufactured shape, the exit aperture extending from the inner surface of the housing wall to the outer surface of the housing wall and through which the LVRC may be withdrawn, the proximal portion of the LVRC extending through the exit aperture and into the coupling zone when in use such that a proximal end of the LVRC is accessible from outside the housing; and wherein the tubular structure comprises an elongate body with a length defined by a cavity end and a coupling end, wherein the cavity end terminates within the cavity and the coupling end terminates at the coupling zone, and wherein the tubular structure is configured to guide the LVRC along the exit path between the cavity end and the coupling end so as to force the LVRC into the delivery shape as the proximal end of the LVRC is withdrawn from the housing.

5. The container as claimed in claim 4, wherein the housing comprises an outer chamber and an inner chamber, the exit aperture connecting the outer chamber with the inner chamber, the inner chamber comprising the cavity suitable for receiving the distal portion of the LVRC, the outer chamber comprising the coupling zone suitable for receiving the proximal end of the LVRC, the outer chamber having a second aperture suitable for receiving open forceps such that the proximal end of the LVRC is accessible with forceps from outside the housing.

6. The container as claimed in claim 4, wherein a cavity portion of the tubular structure defines a guide path which directs the LVRC to the exit aperture.

7. The container as claimed in claim 4, wherein an inner surface of the tubular structure is concave and contiguous with a rim surrounding the exit aperture.

8. The container as claimed in claim 4, wherein the cavity end is configured to be a pivot point configured to apply tension and straighten the LVRC.

9. The container as claimed in claim 4, wherein the guiding surface is planar.

10. The container as claimed in claim 4, wherein the housing contains a spool.

11. The container as claimed in claim 4, wherein the coupling zone is configured to receive open forceps, wherein an inner surface of the coupling zone is contiguous with a rim surrounding the exit aperture.

12. The container as claimed in claim 11, wherein an inner surface of the tubular structure is concave and contiguous with a rim surrounding the exit aperture, and wherein the inner surface of the coupling zone is continuous with the inner surface of the tubular structure.

13. The container as claimed in claim 11, wherein the coupling zone is configured to constrain the open forceps device into only two possible configurations, a first configuration of the open forceps being a 180 degree rotation of a second configuration, so that the open forceps are forced to be centered on and aligned with the proximal end of the LVRC.

14. The container as claimed in claim 13, wherein an inner surface of the coupling zone encloses an oblong rectangular or oval lumen for receiving the open forceps in one of the two possible configurations.

15. The container as claimed in claim 4, wherein the housing is formed of two sections, each section having a rim, and wherein the rims of the sections do not intersect a rim of the exit aperture in the housing through which the LVRC may be withdrawn.

16. The container as claimed in claim 15, wherein the rims of the two sections are configured to fit together in an interference fit so that the two sections are attached to each other.

17. A container for a medical device, comprising:
a housing defining a cavity for receiving a device, a coupling zone external to the cavity, and an exit aperture between the cavity and the coupling zone; and
a substantially straight tubular structure that extends at least partially into the cavity, and wherein the tubular structure, the exit aperture, and the coupling zone define an exit path along which the device can be moved for deployment from the container;
wherein the cavity is approximately cylindrical, and the tubular structure, the exit aperture, and the coupling zone are aligned such that the exit path extends in a direction that is substantially tangential to the cavity.

18. The container as claimed in claim 17, wherein the tubular structure comprises an elongate body with a length defined by a cavity end and a coupling end, wherein the cavity end terminates within the cavity and the coupling end terminates at the coupling zone, wherein the tubular structure extends in the substantially tangential direction between the cavity and the coupling zone, and wherein the tubular structure defines the exit aperture.

19. The container as claimed in claim 18, wherein the cavity end is configured to receive a proximal portion of the device.

20. A container for a medical device, comprising:
a housing defining a substantially unobstructed cavity for receiving a device, a coupling zone external to the cavity, and an exit aperture between the cavity and the coupling zone; and
a substantially straight tubular structure that extends at least partially into the cavity, wherein an inner surface of the tubular structure provides a bearing surface for applying a force to straighten the device, and wherein the tubular structure, the exit aperture and the coupling zone define an exit path along which the device can be moved for deployment from the container.

21. A container for a medical device, comprising:
a housing defining a cavity for receiving the medical device, a coupling zone external to the cavity, and an exit aperture between the cavity and the coupling zone; and
a substantially straight tubular structure that extends at least partially into within the cavity, and wherein the tubular structure, the exit aperture, and the coupling zone define an exit path along which the medical device can be moved for deployment from the container;
wherein the housing in the coupling zone defines a slot through which the exit path extends, the slot defining a restricted space for deployment of a capture device.

22. The container as claimed in claim 21, wherein the housing comprises a transition section with smoothly sloping surfaces inner surfaces for directing the capture device so as to align the capture device with the slot when it is introduced into the coupling zone.

23. The container as claimed in claim 21, further containing the medical device, the medical device comprising a lung volume reduction coil (LVRC) having a proximal portion and a distal portion and having a coiled manufactured shape and a substantially straight delivery shape, wherein the LVRC is in its coiled manufactured shape and the proximal portion lies in the exit path with a proximal end in the coupling zone.

24. The container as claimed in claim 21, wherein the capture device is a forceps.

* * * * *